United States Patent
O'Lenick, Jr.

[11] Patent Number: 6,004,542
[45] Date of Patent: Dec. 21, 1999

[54] SILICONE SALICYLATE ESTERS

[75] Inventor: Anthony J. O'Lenick, Jr., Dacula, Ga.

[73] Assignee: Hansotech Inc, Woodbury, N.Y.

[21] Appl. No.: 09/215,806

[22] Filed: Dec. 18, 1998

Related U.S. Application Data

[63] Continuation-in-part of application No. 09/040,431, Mar. 18, 1998, Pat. No. 5,908,949, which is a continuation-in-part of application No. 09/039,435, Mar. 16, 1998, Pat. No. 5,883,279.

[51] Int. Cl.$^6$ ...................................................... A61K 7/00
[52] U.S. Cl. ............................ 424/60; 424/70.9; 556/437
[58] Field of Search ...................... 424/60, 70.9; 556/437

[56] References Cited

U.S. PATENT DOCUMENTS

| | | |
|---|---|---|
| 5,061,479 | 10/1991 | Grollier et al. ............................ 424/47 |
| 5,223,249 | 6/1993 | Forestier et al. ........................... 424/59 |
| 5,296,625 | 3/1994 | O'Lenick, Jr. . |
| 5,714,134 | 2/1998 | Richard et al. ............................ 424/59 |
| 5,741,480 | 4/1998 | Ascione ..................................... 424/59 |
| 5,883,279 | 3/1999 | O'Lenick, Jr. .......................... 556/437 |
| 5,900,231 | 5/1999 | Richard et al. ............................ 424/60 |
| 5,906,812 | 5/1999 | Richard et al. ............................ 424/60 |
| 5,908,949 | 6/1999 | O'Lenick, Jr. .......................... 556/437 |

*Primary Examiner*—Paul F. Shaver

[57] ABSTRACT

The invention discloses novel salicylate esters made by reacting (a) a carboxy silicone, and (b) the hydroxyl group of salicylic acid. The compounds of the invention by virtue of (i) the silicone group, (ii) the salicylate group group and (iii) the polyoxyalkylene present in the compound are extremely efficient skin care compounds used in topical treatment of skin.

7 Claims, No Drawings

SILICONE SALICYLATE ESTERS

RELATED APPLICATIONS

This application is a continuation in part of application Ser. No. 40,431 filed Mar. 18, 1998, now U.S. Pat. No. 5,908,949 issued Jun. 1, 1999, which is in turn a continuation in part of application Ser. No. 039.435 filed Mar. 16, 1998, now U.S. Pat. No. 5.883,279 issued Mar. 16, 1999.

The invention discloses novel salicylate esters of silicone compounds which an ester linkage, and a silicone polymer. Compounds of the invention are made by reacting (a) a carboxy silicone, and (b) salicylic acid to form an ester. Compounds of the invention by virtue of (i) the silicone group, (ii) the ester group and (iii) the ultra violet absorbing group salicylic group, the compounds are effective durable ultra-violet absorbers.

The reaction used to prepare the compounds of the present invention is an esterification of a carboxy silicone and salicylic acid. The resulting ester provides ultra violet absorbance and is durable to substrates like textile fabrics, hair and skin.

ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second: since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

Silicone oils do not provide ultra violet absorption, and consequently protection from the damaging effects of the sun. The aromatic compounds that provide this type of absorbance are not durable to the surfaces of substrates.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

THE INVENTION

OBJECT OF THE INVENTION

It is the object of the present invention to provide a durable ultra violet protection to substrates like skin, hair and textile fabrics and fibers, as well as rubber and plastics. The presence of silicone in the molecule gives superior durability to these substrates, the presence of the salicylic group gives superior ultra violet protection and the introduction of the ester linkage between the silicone and aromatic group results in a linkage which will biodegrade rapidly in waste water, making the compound less persistent in the waste water stream.

The formation of the ester linkage and the incorporation of the salicylic group into the silicone of the present invention is accomplished by an esterification reaction of a carboxy silicone and salicylic acid.

SUMMARY OF THE INVENTION

The compounds of this invention are made by the esterification of a carboxy silicone compound and salicylic acid. In order to obtain a molecule with the desired attributes, the aromatic compound must be mono-hydroxyl. This prevents crosslinking with the carboxy silicone, and formation of a polyester. The polyester is undesirable. The second requirement is that the aromatic compound chosen must have ultra violet absorbance. Salicylic acid meets both requirements.

Only if the compounds are specifically selected will compounds useful in the preparation of the compounds of the present invention be obtained.

Specifically, the compounds of the present invention are esters compounds which is prepared by the esterification reaction of;

(a) a silicone carboxylate conforming to the following structure:

$$R'-\underset{\underset{Me}{|}}{\overset{\overset{Me}{|}}{Si}}-O-\left[\underset{\underset{R}{|}}{\overset{\overset{Me}{|}}{Si}}-O\right]_o-\left[\underset{\underset{R^1}{|}}{\overset{\overset{Me}{|}}{Si}}-O\right]_q-\underset{\underset{Me}{|}}{\overset{\overset{Me}{|}}{Si}}-R'$$

wherein;

Me is methyl;

R and R' are $CH_3$ or $$-(CH_2)_3-O(EO)_a-(PO)_b-(EO)_c-C(O)-R''-C(O)-OH;$$

with the proviso that both R and R' are not $CH_3$;

R" is selected from $$-CH_2-CH_2-;\quad -CH=CH-;\quad -CH_2-C(R^7)-H;$$

[cyclohexadiene structure] and [tetrachlorobenzene structure];

$R^7$ is alkyl having from 1 to 20 carbon atoms;

$R^1$ is selected from lower alkyl $CH_3(CH)_n-$ or phenyl;

n is an integer from 0 to 8;

a, b and c are integers independently ranging from 0 to 20;

EO is an ethylene oxide residue $-(CH_2CH_2-O)-$;

PO is a propylene oxide residue $-(CH_2CH(CH_3)-0)-$;

o is an integer ranging from 1 to 100;

q is an integer ranging from 0 to 500.

and (b) salicylic acid which conforms to the following structure:

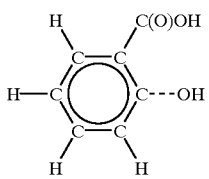

Compounds of the present invention conform to the following structure:

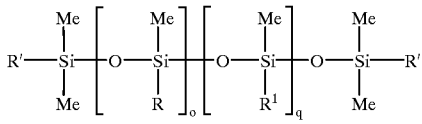

wherein;
Me is methyl;
R and R' are $CH_3$ or $$-(CH_2)_3-O-(EO)_a-(PO)_b-(EO)_c-C(O)-R''-C(O)-OR^2;$$

with the proviso that both R and R' are not $CH_3$;
R" is selected from

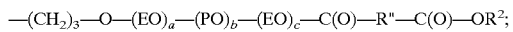

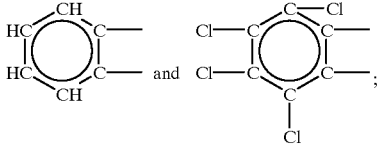

$R^7$ is alkyl having from 1 to 20 carbon atoms;
$R^1$ is selected from lower alkyl $CH_3(CH)_n-$ or phenyl;
n is a n integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500:
$R^2$ is;

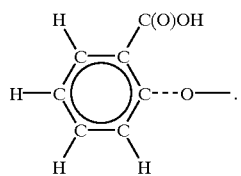

EXAMPLES

The compounds of the present invention are prepared by the reaction of a carboxy silicone compound and salicylic acid.
Examples of suitable reactants are as follows;
All percentages given are based upon percent by weight, based upon the total weight of the entire batch. All temperatures are degrees C.
Reactants
Salicylic Acid
Salicylic acid is 2-hydroxybenzoic acid.

Carboxy Reactants
The carboxy silicone compounds useful as raw materials in the preparation of the compounds of the present invention are disclosed in U.S. Pat. No. 5,296,625 to O'Lenick, Jr. et al, incorporated herein by reference.

REFERRED EMBODIMENTS

In another preferred embodiment x+y+z is greater than zero.
In another preferred embodiment R" is $-CH_2-CH_2-$
In another preferred embodiment R" is $-CH_2-C(R^7)-$H.
In another preferred embodiment R" is

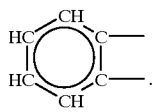

In another preferred embodiment R" is

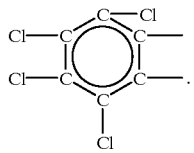

EXAMPLES
Dimethicone Carboxylate Compounds
Dimethicone Carboxylate compounds are disclosed in U.S. Pat. No. 5,296,625 incorporated herein by reference. They marketed by Lambent Technologies Inc, a Petroferm Company under the Lambentlube trade name. The compounds conform to the following structure;

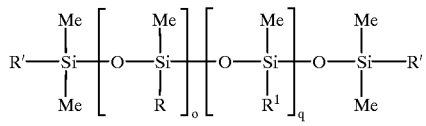

wherein;
Me is methyl;
R and R' are $CH_3$ or $$-(CH_2)_3-O-(EO)_a-(PO)_b-(EO)_c-C(O)-R''-C(O)-OH;$$

with the proviso that both R and R' are not $CH_3$;
R" is selected from

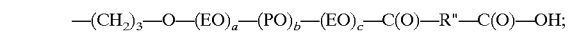

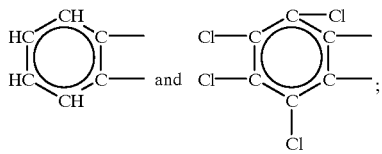

$R^7$ is alkyl having from 1 to 20 carbon atoms;
$R^1$ is selected from lower alkyl $CH_3(CH)_n-$ or phenyl;
n is an integer from 0 to 8;
a, b and c are integers independently ranging from 0 to 20;

EO is an ethylene oxide residue —$(CH_2CH_2-O)$—;
PO is a propylene oxide residue —$(CH_2CH(CH_3)-O)$—;
o is an integer ranging from 1 to 100;
q is an integer ranging from 0 to 500.

The carboxy reactants are defined in O'Lenick U.S. Pat. No. 5,296,625 incorporated herein by reference, examples 15–32.

R" Definition

I) O'Lenick Reactant Example I (Succinic Anhydride)

R"is —$H_2C-CH_2$—

II) O'Lenick Reactant Example II (Alkyl Succinic Anhydride)

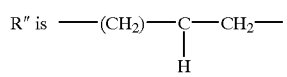
R" is —$(CH_2)$—C—$CH_2$—
          |
          H

III) O'Lenick Reactant Example III (Alkyl Succinic Anhydride)

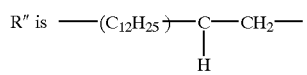
R" is —$(C_{12}H_{25})$—C—$CH_2$—
          |
          H

IV) O'Lenick Reactant Example IV (Alkyl Succinic Anhydride)

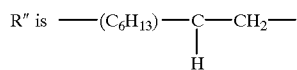
R" is —$(C_6H_{13})$—C—$CH_2$—
          |
          H

V) O'Lenick Reactant Example V (Alkyl Succinic Anhydride)

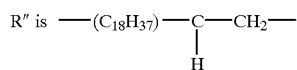
R" is —$(C_{18}H_{37})$—C—$CH_2$—
          |
          H

VI) O'Lenick Reactant Example VI (Alkyl Succinic Anhydride)

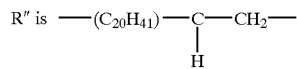
R" is —$(C_{20}H_{41})$—C—$CH_2$—
          |
          H

VII) O'Lenick Reactant Example VII (Maleic Anhydride)

R" is —HC=CH—

VIII) O'Lenick Reactant Example VIII (Phthalic Anhydride)

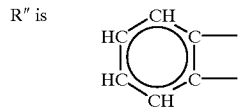

IX) O'Lenick Reactant Example IX (Tetrachlorophthalic anhydride)

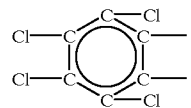
R" is

Compounds of the Present Invention

General Reaction Conditions;

The esterification can be run without catalyst; however, when no catalysts used reaction rates are less efficient. Standard esterification catalysts are generally used at concentrations of between 0.05% to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C under an inert nitrogen blanket. The nitrogen blanket preserves the color. Preferred temperature range is between 180 and 210 C. Water is removed from the reaction which is done using a nitrogen sparge or vacuum.

Examples 1–10

General Procedure

Into a suitable round bottom, three neck flask equipped with a Dean Stark trap, a thermometer and a nitrogen sparge is added the specified number of grams of the carboxy silicone and the specified number of grams of fatty alcohol alkoxylate and 0.25% of total weight of the batch of catalyst. The reaction mass is blanketed with nitrogen, and heated to 180 and 200 C under an inert nitrogen blanket. Once the reaction temperature reaches 120 C water begins to boil off and is collected in the Dean Stark Trap. Within four to five hours the theoretical water is collected off and the acid value is very low. The product is used without additional purification.

Example 1

Into a suitable round bottom, three neck flask equipped with a Dean Stark trap, a thermometer and a nitrogen sparge is added the specified number of grams of the carboxy silicone), 137.0 grams of salicylic acid and 0.25% of total weight of the batch of catalyst. The reaction mass is blanketed with nitrogen, and heated to 180 and 200 C under an inert nitrogen blanket. Once the reaction temperature reaches 120 C water begins to boil off and is collected in the Dean Stark Trap. Within four to five hours the theoretical water is collected off and the acid value is very low. The product is used without additional purification.

Example 2–10

Example 1 is repeated only this time substituting the specified number of grams of the specified carboxy silicone for the carboxy silicone specified;

Note; In the below table Gms. is grams

| | Carboxy Silicone Compound | | |
|---|---|---|---|
| Example | R" Definition | O'Lenick Example | Grams |
| 2 | I | 15 | 2,429.0 |

-continued

| Example | Carboxy Silicone Compound R" Definition | O'Lenick Example | Grams |
|---|---|---|---|
| 3 | II | 16 | 2,147.0 |
| 4 | III | 17 | 5,398.0 |
| 5 | IV | 18 | 533.0 |
| 6 | V | 19 | 4,723.0 |
| 7 | VI | 20 | 3,083.0 |
| 8 | VII | 21 | 3,648.8 |
| 9 | VIII | 22 | 1,722.4 |
| 10 | IX | 23 | 1,288.0 |

What is claimed:

1. A process for protecting hair and skin which comprises contacting the skin with an effective ultra violet protecting amount of a compound conforming to the following structure:

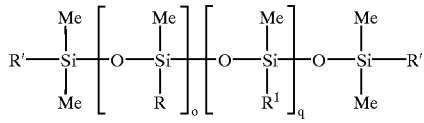

wherein;

Me is methyl;

R and R are $CH_3$ or $$-(CH_2)_3-O-(EO)_a-(PO)_b-(EO)_c-C(O)-R''-C(O)-R^2;$$

with the proviso that both R and R' are not $CH_3$;

R" is selected from

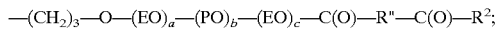

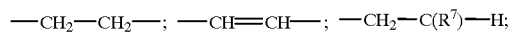

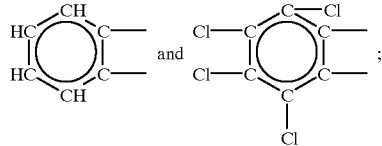

$R^7$ is alkyl having from 1 to 20 carbon atoms;
$R^1$ is selected from lower alkyl $CH_3(CH)_n$— or phenyl;

n is an integer from 0 to 8;
a, b and c are integers independently ranging from 0 to 20;
EO is an ethylene oxide residue $-(CH_2CH_2-O)-$;
PO is a propylene oxide residue $-(CH_2CH(CH_3)-O)-$;
o is an integer ranging from 1 to 100;
q is an integer ranging from 0 to 500;
$R^2$ is;

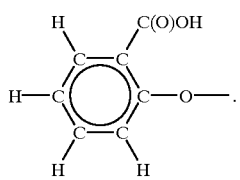

2. A process of claim 1 wherein R" is $-CH_2-CH_2-$.
3. A process of claim 1 wherein R" is $-CH_2-C(R^7)-H$.
4. A process of claim 1 wherein R" is

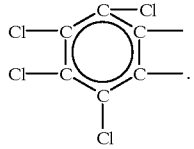

5. A process of claim 1 wherein R" is

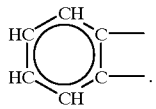

6. A process of claim 3 wherein $R^7$ is alkyl having from 6 to 20 carbon atoms.
7. A process of claim 3 wherein $R^7$ is alkyl having from 12 to 20 carbon atoms.

* * * * *